United States Patent [19]

Lewis et al.

[11] Patent Number: 5,301,690
[45] Date of Patent: Apr. 12, 1994

[54] DEVICE FOR CONTAINING BODILY FLUID RESULTING FROM THE OCCURRENCE OF A RUPTURE OR LEAK DURING A MEDICAL PROCEDURE

[76] Inventors: Edmund J. Lewis, 680 N. Lakeshore Dr., Suite 724, Chicago, Ill. 60611; Stephen M. Korbet, 1867 N. Halsted St., Chicago, Ill. 60614

[21] Appl. No.: 917,349

[22] Filed: Jul. 23, 1992

[51] Int. Cl.⁵ ............................................. A61F 5/37
[52] U.S. Cl. .................................... 128/877; 2/16; 2/59; 128/849; 604/327
[58] Field of Search .................. 128/849, 877, 878; 602/3; 2/16, 59, DIG. 11; 604/4-6, 327

[56] References Cited

U.S. PATENT DOCUMENTS

| | | | |
|---|---|---|---|
| 2,059,136 | 10/1936 | Moller | 2/59 |
| 3,628,813 | 12/1971 | Lee et al. | 604/4 |
| 3,722,508 | 3/1973 | Roberts | 128/877 |
| 4,079,007 | 3/1978 | Hutchisson . | |
| 4,083,777 | 4/1978 | Hutchisson . | |
| 4,381,775 | 5/1983 | Nose et al. | 604/6 |
| 4,453,933 | 6/1984 | Speaker | 128/877 |
| 4,470,410 | 9/1984 | Elliott | 128/877 |
| 4,610,245 | 9/1986 | Biearman | 128/877 |
| 4,772,275 | 9/1988 | Erlich . | |
| 4,822,341 | 4/1989 | Colone | 604/4 |
| 4,828,543 | 5/1989 | Weiss et al. | 604/6 |
| 4,856,112 | 8/1989 | Effle | 2/16 |
| 4,857,043 | 8/1989 | Benjamin | 604/6 |
| 4,911,151 | 3/1990 | Rankin et al. | 602/3 |
| 4,913,813 | 4/1990 | Covarrubias et al. . | |
| 4,959,875 | 10/1990 | Moon | 2/16 |
| 4,977,622 | 12/1990 | Schley | 2/59 |
| 4,995,857 | 9/1990 | Shettigar | 604/4 |
| 4,998,538 | 3/1991 | Charowsky et al. . | |
| 5,063,919 | 11/1991 | Silverberg | 2/16 |
| 5,074,838 | 12/1991 | Kroyer | 604/4 |
| 5,116,308 | 5/1992 | Hagiwara | 604/4 |
| 5,120,302 | 6/1992 | Vescovini et al. | 604/6 |
| 5,131,412 | 7/1992 | Rankin | 128/877 |
| 5,143,762 | 9/1992 | Ho | 2/16 |
| 5,178,162 | 1/1993 | Bose | 128/849 |

FOREIGN PATENT DOCUMENTS

| | | | |
|---|---|---|---|
| 0128715 | 1/1929 | Switzerland | 2/59 |
| 2245477 | 1/1992 | United Kingdom | 2/16 |

Primary Examiner—David Isabella
Assistant Examiner—Gina M. Gualtieri
Attorney, Agent, or Firm—Burns, Doane, Swecker & Mathis

[57] ABSTRACT

An enclosure used in conjunction with an extracorporeal medical device for containing bodily fluid resulting from the occurrence of a rupture or leak during medical treatment includes a sleeve having an interior for receiving and surrounding the medical device. The sleeve is provided with two openings positioned at opposite ends of the sleeve for allowing tubing connected to the medical device to extend out of the sleeve. Each of the openings can be provided with an adhesive for closing the opening once the medical device is positioned in the interior of the sleeve to thereby define a closed environment within the interior of the sleeve. In accordance with another aspect of the invention, an enclosure for surrounding a portion of a patient's body that serves as an access site for accessing the patient's bodily fluid includes a sleeve having an interior. The sleeve is provided with open ends that allow a portion of the patient's body on opposite sides of the access site and tubing extending from the access site to extend out of the sleeve. An elastic band surrounds each of the openings so that the portion of the sleeve adjacent each opening closely contacts and surrounds the tubing as well as the portion of the patient's body extending through the opening.

18 Claims, 3 Drawing Sheets

DEVICE FOR CONTAINING BODILY FLUID RESULTING FROM THE OCCURRENCE OF A RUPTURE OR LEAK DURING A MEDICAL PROCEDURE

FIELD OF THE INVENTION

Generally speaking, the present invention pertains to an enclosure for use during a medical procedure. More particularly, the present invention relates to a sleeve for surrounding and enclosing an extracorporeal medical device to contain bodily fluid such as blood resulting from the occurrence of a rupture or leak during a medical procedure. The present invention also relates to a sleeve for surrounding and enclosing the site of vascular access on a patient's body during a medical procedure for containing bodily fluid such as blood resulting from the occurrence of a rupture or leak during a medical procedure.

BACKGROUND OF THE INVENTION

There are many types of medical procedures involving the removal of bodily fluid from a patient's body. One example of such a medical procedure is hemodialysis treatment. Hemodialysis treatment has been used for many years as a way of treating renal disease and has proven quite useful in providing artificial kidney functions for individuals whose natural kidney functions are impaired. Typically, hemodialysis treatment involves the use of a hemodialysis filter unit, i.e., a dialyzer, that serves as the artificial kidney. Blood that contains waste substances is pumped out of the patient's blood vessel and into the dialyzer which is comprised of a plurality of small plastic tubes or capillaries. These capillaries are bathed with a dialysate solution that is pumped into the dialyzer. As a result, the blood is exposed to diffusive equilibration, thereby resulting in the removal of toxic substances from the blood. The filtered blood then flows out of the dialyzer and is returned to the patient.

Although hemodialysis treatment has been found to be an effective way of treating individuals that lack normal kidney functions, there are problems associated with the procedure. For example, during hemodialysis treatment, the blood is typically pumped out of the patient's body at a rate of between 200–500 ml/min and the pressure within the dialyzer can be as high as 300 mmHg. Given this flow rate of the blood and pressure within the dialyzer, defects in the tubing carrying the patient's blood and defects in the connectors that connect the tubing to the dialyzer are particularly problematic since such defects can result in the patient's blood being sprayed out of the dialyzer. This rupture or leak can take the form of a pressurized or aerosolized stream of blood.

Related problems can also arise at the site of vascular access to the patient's body. In order to gain access to the blood of a patient who requires artificial kidney treatment, a variety of procedures are available for allowing blood to be pumped out of the patient's body and into the dialyzer. The most frequent procedure involves the use of needles which are placed in blood vessels, or a vascular graft which has been placed in the patient's arm. These needles are attached to blood tubing and the blood tubing is connected to the dialyzer. On occasion, a leak or rupture may arise at the site of vascular access, or disconnection of the blood tubing from the needles may occur. This problem is compounded by the fact that the blood is being pumped under pressure at a relatively high flow rate.

The occurrence of ruptures or leaks during the hemodialysis procedure presents particular problems since persons in the area can be exposed to the risk of infectious disease. If the patient undergoing hemodialysis treatment has hepatitis, or is a carrier of a hepatitis virus, or is infected by the HIV virus or some other communicable disease, the individual exposed to the blood rupture or leak may be in serious danger of being infected by such diseases. Such hemodialysis treatment is typically provided in a hemodialysis facility in which several patients being cared for are located in close proximity to one another, the risk associated with a potential rupture is particularly acute.

The possibility that individuals in the vicinity of the hemodialysis procedure, including staff and other individuals, may be exposed to infectious diseases has led to the implementation of protective measures in an attempt to prevent individuals in the area of the hemodialysis treatment from being subjected to infectious diseases. Indeed, the Occupational Safety and Health Administration issued and published final regulations in December 1991 concerning protective devices that must be used by health care workers and others with respect to bloodborne pathogens. The protections to be offered are characterized in the regulations as engineering devices and work practice controls. Engineering devices include such things as personal protection equipment (i.e., gowns, masks, etc.) while work practice controls involve education and other types of measures.

Typically, dialysis facilities require that individuals involved in providing hemodialysis treatment wear gloves, gowns and protective facial devices. However, implementation and enforcement of these protective procedures (i.e., ensuring that all individuals in the vicinity of the hemodialysis treatment adhere to the protective procedures) can be somewhat difficult.

SUMMARY OF THE INVENTION

The present invention addresses the foregoing problems associated with bodily fluid leakage an rupture during a medical procedure, such as hemodialysis, by providing, in accordance with one aspect of the present invention, an enclosure for enclosing an extracorporeal medical device. The enclosure comprises a sleeve having an interior. The sleeve is adapted to surround the extracorporeal medical device so that the device is located in the interior of the sleeve, whereby bodily fluid resulting from the occurrence of a rupture or a leak during a medical procedure is contained within the sleeve. The sleeve can be provided with two oppositely positioned openings such that tubing which is connected to the inlet and the outlet of the medical device extends through the openings in the sleeve.

In the preferred embodiment of the present invention, each of the two openings in the sleeve is provided with an arrangement for closing the opening so that the portion of the sleeve adjacent each opening contacts and tightly surrounds the tubing to thereby inhibit bodily fluid from escaping from the interior of the sleeve. Further, the sleeve can be provided with two ports positioned along one side of the sleeve so that inlets and outlets which form a part of the medical device can be connected to tubing. The sleeve can also be provided with tubing retainers for retaining the tubing and a tear line for permitting access to the interior of the sleeve.

In accordance with another aspect of the present invention, an enclosure is provided for use during a medical procedure to surround a portion of a patient's body that serves as an access site for accessing the patient's bodily fluid (e.g., blood) and to contain bodily fluid resulting from the occurrence of a rupture or leak in the vicinity of the access site. The enclosure comprises a sleeve having an interior and two oppositely positioned openings for allowing a portion of the patient's body on opposite sides of the access site and tubing extending from the access site to extend out of the sleeve.

In accordance with a preferred embodiment of the present invention, each of the openings can be provided with an elastic band that surrounds the opening and that tends to cause the size of the opening to be reduced so that when the sleeve is placed on the patient's body the elastic band causes the portion of the sleeve adjacent each opening to closely contact and surround the tubing and the portion of the patient's body extending through the opening, thereby defining a closed environment within the interior of the sleeve so that bodily fluid does not escape from the interior of the sleeve. The sleeve can be provided with a tear line that extends across at least a portion of the sleeve for allowing access to the interior of the sleeve. Additionally, a tubing retainer can be positioned adjacent each one of the two openings in the sleeve for encircling at least a portion of the outer surface of the tubing to thereby retain the tubing in place within the sleeve.

In accordance with a further aspect of the present invention, a method of containing bodily fluid resulting from the occurrence of a rupture or leak during a medical procedure comprises the steps of: providing a sleeve having an interior and two openings that are positioned adjacent opposite ends of the sleeve; positioning the sleeve relative to a place of potential bodily fluid rupture or leak such that the sleeve surrounds and encloses the place of potential bodily fluid rupture or leak; and sealing access through the two openings in the sleeve to define a substantially closed environment within the sleeve so that bodily fluid resulting from the occurrence of a rupture or leak during the medical procedure is contained within the sleeve and is inhibited from escaping from the sleeve.

In one respect, the sleeve can be positioned relative to an extracorporeal medical device so that the sleeve surrounds and encloses the medical device and so that tubing connected to the device extends through each of the openings in the sleeve. The step of sealing access through the two openings in the sleeve can be carried out by providing an adhesive on the inner surface of the sleeve adjacent each of the two openings and closing each of the openings through use of the adhesive such that the portion of the sleeve adjacent each of the openings closely contacts and surrounds the tubing extending through the sleeve.

In another respect, the sleeve can be positioned with respect to the site of vascular access on a patient's body in such a manner that the sleeve surrounds and encloses the site of vascular access and so that a portion of the patient's body extends through each of the openings. In order to seal access through the two openings in the sleeve, the sleeve can be provided with elastic bands adjacent each of the openings whereby the elastic bands tend to reduce the size of the openings in the sleeve s that the portion of the sleeve located adjacent each opening closely contacts and surrounds a portion of the patient's body extending through each opening as well as tubing extending between the site of vascular access and the medical device.

The present invention provides an extremely effective solution to the problem of inadvertent bodily fluid ruptures and leaks that may arise during a medical procedure. In a relatively inexpensive and simple manner, the present invention affords protection to an otherwise unprotected group of individuals—the other patients in the treatment facility. Moreover, while individuals administering the treatment are protected to a certain degree by protective measures currently in use (i.e., gloves, gowns and protective facial devices), the present invention provides an additional measure of protection for those individuals.

BRIEF DESCRIPTION OF THE DRAWING FIGURES

The features and characteristics of the present invention will become more apparent from the description that follows considered in conjunction with the drawing figures in which like elements are designated by like reference numerals and wherein.

DETAILED DESCRIPTION OF THE PREFERRED EMBODIMENTS

The preferred embodiment of the dialyzer enclosure and the vascular access sleeve according to the present invention will be described, for illustrative purposes, in connection with a hemodialysis system. However, it is to be understood that the dialyzer enclosure and the vascular access sleeve have applications in conjunction with any type of extracorporeal medical device and in any type of medical procedure in which bodily fluid is removed from a patient's body.

Figure 1:
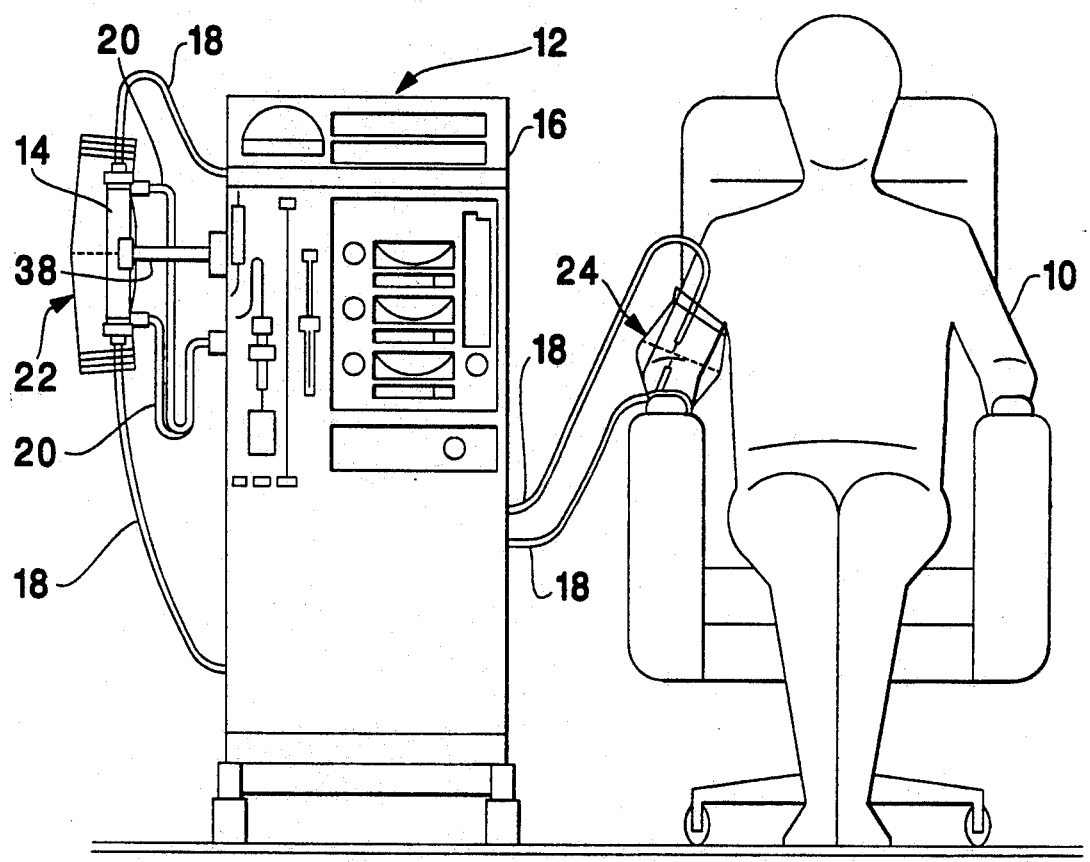
FIG. 1 is a schematic illustration of a patient undergoing hemodialysis treatment and shows the dialyzer enclosure and the vascular access enclosure of the present invention.

With reference initially to FIG. 1, a patient 10 is shown connected to a hemodialysis system 12 during a typical hemodialysis procedure. The hemodialysis system 12 includes a hemodialysis filter unit or dialyzer 14 that is connected to an enclosure unit 16 which houses all of the necessary features and components, including the monitoring and output displays, that are necessary for proper operation of the hemodialysis system. The features of the enclosure unit 16 will not be described in detail here since they are conventional and known to persons of ordinary skill in the art.

The hemodialysis system 12 also includes blood tubing 18 that extends from the site of vascular access on the patient 10, such as the patient's arm, to the dialyzer 14. Additionally, dialysate tubing 20 extends from the enclosure unit 16 to the dialyzer 14 for conveying dialysate solution from the enclosure unit 16 to the dialyzer 14, and for conveying dialysate solution from the dialyzer 14 back to the enclosure unit 16.

The dialyzer enclosure 22 according to the present invention is shown in position in FIG. 1 in surrounding relation with respect to the dialyzer 14. Additionally, the vascular access enclosure 24 according to the present invention is also illustrated in position in surrounding relation to the site of vascular access on the patient's body.

Figure 2:
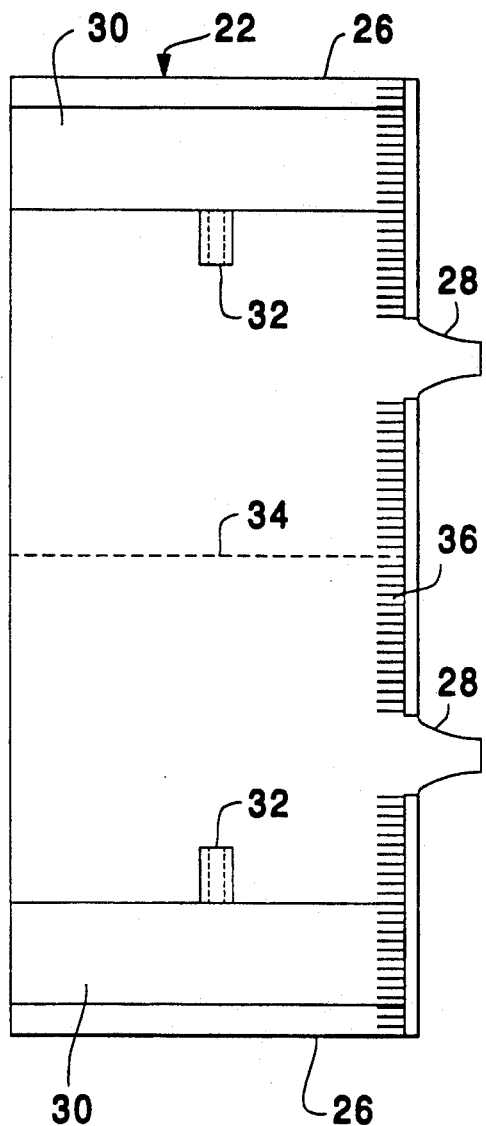
FIG. 2 is a plan view of the dialyzer enclosure according to the present invention.

Turning to FIG. 2, the dialyzer enclosure 22 according to the present invention is comprised of a sleeve of material that is specifically sized and configured to surround and enclose the dialyzer 14. The sleeve 22 is provided with open ends to thereby define two openings 26 that are positioned at opposite ends of the sleeve 22. In the preferred embodiment, the openings 26 extend across the entire width of the sleeve in order to permit easy access to the interior of the sleeve. However, it may be desirable in some instances to provide openings 26 that extend over only a portion of the width of the sleeve 22.

The sleeve 22 is also provided with two ports 28, the purpose of which will become apparent from the description below. The ports 28 extend through the sleeve so as to provide a through opening. The two ports 28 are preferably positioned along one side of the sleeve 22 and preferably extend outwardly away from the interior of the sleeve 22 to define cylindrical extensions.

An adhesive strip 30 is positioned at each end of the sleeve 22 adjacent each of the openings 26. The adhesive strips 30 allow the openings 26 at each end of the dialyzer sleeve 22 to be closed once the dialyzer 14 is positioned in the interior of the dialyzer sleeve 22. In this way, access through the openings 26 can be sealed. The adhesive strips 30 can be any suitable type of adhesive that allows the openings 26 to be securely closed so that the interior of the sleeve 22 is substantially sealed from the outside environment. The adhesive selected can depend upon the particular type of material from which the dialyzer sleeve 22 is fabricated. For example, a Scotch TM tape type of adhesive could be employed. Also, closing arrangements other than adhesive could be employed to seal access through the openings 26. Further, it may be desirable in some instances to utilize an adhesive that permits the openings 26 to be selectively opened and closed.

Positioned on the inner surface of the sleeve 22 are two tubing retainers 32. The tubing retainers 32 allow the blood tubing that is connected to the dialyzer 14 to be securely retained in position within the dialyzer sleeve 22. The tubing retainers 32 can take the form of a generally C-shaped member that encircles at least a portion of the outer periphery of the blood tubing. However, other suitable devices could be employed to retain the blood tubing in place within the interior of the sleeve 27.

The dialyzer sleeve 22 can also be provided with a tear line 34 that extends across the width of the dialyzer sleeve 22. The tear line 34 is constructed in such a manner that by simply pressing on the tear line 34, an opening will be formed in the sleeve 22. Thus, the tear line 34 allows easy access to the interior of the dialyzer sleeve 22 should it become necessary. At the same time, the tear line 34 is constructed to ensure that the liquid tightness of the sleeve is not adversely impacted. It is, of course, possible to provide a tear line that extends across only a portion of the width of the dialyzer sleeve 22.

The dialyzer sleeve 22 can also include a sealed edge 36 that extends along one side of the dialyzer sleeve 22. This allows the dialyzer sleeve 22 to be fabricated as a generally rectangular sheet of material. After fabrication, the two edges of the sheet of material can then be sealed to one another along the sealed edge 36. If desired, the formation of the sealed edge 36 can take place after the dialyzer has been placed within the sleeve so that the sleeve surrounds the dialyzer. The sealed edge 36 is formed in such a way as to permit access through the ports 28. Of course, it is also envisioned that the dialyzer sleeve 22 could be fabricated to have the same configuration shown in FIG. 2, except without the sealed edge 36.

Figure 3:
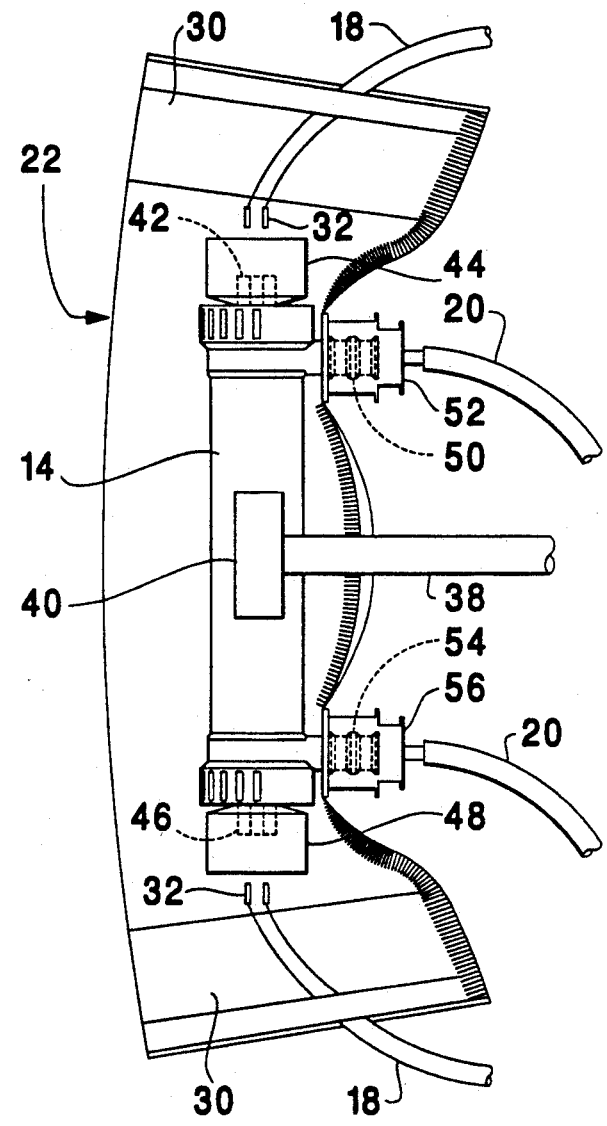
FIG. 3 is a plan view of the dialyzer enclosure according to the present invention in use on the hemodialysis filter unit.

Turning to FIG. 3 it can be readily seen how the dialyzer sleeve 22 according to the present invention is employed. Initially, the hemodialysis filter unit or dialyzer 14 is positioned within the interior of the dialyzer sleeve 22. The dialyzer 14 is supported on a support arm 38 that extends from the enclosure unit 16. The support arm 38 is provided with a clamp 40 that is clamped to the dialyzer 14. The clamp 40 preferably clamps the dialyzer 14 exteriorly of the dialyzer sleeve 22 so that the support arm 38 and the clamp 40 do not penetrate the sleeve 22.

The blood tubing 18 that conveys blood from the patient to the dialyzer 14 is connected to a blood inlet 42 of the dialyzer 14 by way of a connector 44. Similarly, the blood tubing 18 that conveys filtered blood from the dialyzer 14 to the patient is connected to a blood outlet 46 of the dialyzer 14 by way of a connector 48. The blood tubing 18 is retained in place within the interior of the sleeve 22 through use of the tubing retainers 32.

Similarly, the dialysate tubing 20 that conveys dialysate solution to the dialyzer 14 is connected to a dialysate inlet 54 by way of a connector 56. Further, the tubing 20 which conveys dialysate solution from the dialyzer 14 to the enclosure unit 16 is connected to a dialyzer outlet 50 of the dialyzer 14 by way of a connector 52. The ports 28 which form a part of the dialyzer sleeve 22 preferably encircle the dialysate inlet 50 and the dialysate outlet 54 s that when the connectors 52, 56 are connected to the dialyzer inlet 50 and the dialyzer outlet 54, access through the ports 28 is effectively sealed. As a result, a seal is provided which does not permit blood in the interior of the dialyzer sleeve 22 from escaping through the ports 28.

Once the dialyzer 14 is positioned within the interior of the dialyzer sleeve 22 with the blood tubing 18 connected to the dialyzer 14, the open ends 26 of the dialyzer sleeve 22 can be closed through use of the adhesive strips 30 located at either end of the dialyzer sleeve 22. The adhesive strips 30 allow the openings 26 to be closed and the dialyzer sleeve 22 tightly sealed so to define a substantially closed environment within the interior of the dialyzer sleeve 22. The adhesive strips 30 also adhere to the blood tubing 18 and thus contribute to maintaining the position of the blood tubing 18.

It can be readily appreciated, therefore, that the dialyzer sleeve 22 according to the present invention completely surrounds, encloses and envelopes the dialyzer 14. If a rupture or leak should occur during the hemodialysis procedure, such as in the region of the connectors 44, 48, the blood will be completely contained within the interior of the dialyzer sleeve 22 until corrective measures can be instituted. Thus, there is no immediate risk that individuals in the vicinity during the hemodialysis procedure will be exposed to infectious diseases that may be present in the patient's blood.

The dialyzer sleeve 22 can be fabricated from a flexible, transparent material that is impervious to fluid. By fabricating the sleeve of transparent material, an individual can readily determine through visual inspection that a blood leak or rupture has occurred. Preferably, the dialyzer sleeve 22 is fabricated from a suitable thin gauge plastic material.

Figure 4:
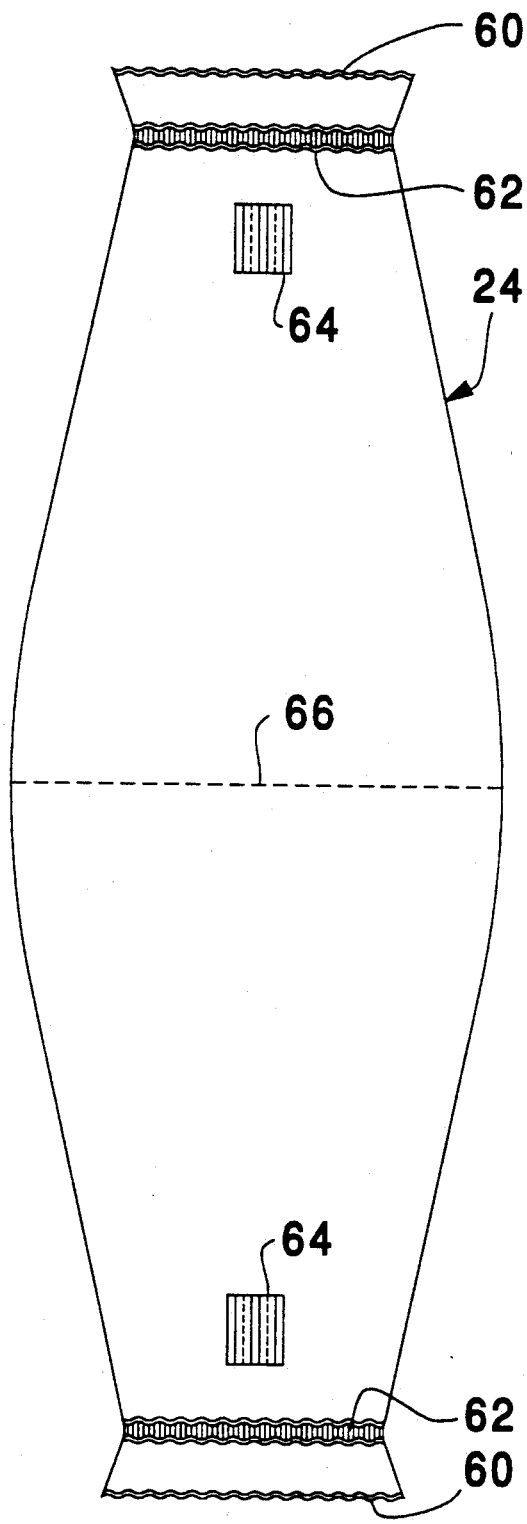
FIG. 4 is a plan view of the vascular access enclosure according to the present invention.

Turning to FIG. 4, the features of the vascular access enclosure 24 according to the present invention can be seen. Like the dialyzer enclosure 22, the vascular access enclosure 24 can be fabricated as a one piece, integral unitary sleeve. The ends of the sleeve 24 are open so as to provide oppositely positioned openings 60 in the sleeve. The openings 60 permit the portion of the patient's body on either side of the site of vascular access to extend out of the sleeve 24. The openings 60 also allow the blood tubing which conveys blood away from the site of vascular access and which returns filtered blood to the patient's body to extend out of the sleeve 24.

Each end of the vascular access sleeve 24 is also provided with an elastic band 62. These elastic bands 62 are positioned adjacent the open ends 60 of the vascular access sleeve 24 and tend to reduce the size of the openings 60 so that the portion of the sleeve 24 adjacent each opening 60 or end of the sleeve 24 closely contacts and tightly surrounds the portion of the patient's body extending through the openings 60.

A double tubing retainer 64 can be secured to the inner surface of the vascular access sleeve 24 adjacent each of the openings 60 to secure in place the blood tubing extending from the site of vascular access on the patient's body. Each of the double tubing retainers 64 is designed to secure two tubes in place within the vascular access sleeve 24 since, in some instances, it may be necessary to have tubes in addition to the blood tubing extending out of the vascular access sleeve 24. The double tubing retainer 64 can comprise two side by side generally C-shaped members that are designed to encircle at least a portion of the outer periphery of the tubing. It is to be understood, however, that single tubing retainers such as those provided on the dialyzer sleeve 22 could also be employed.

The vascular access sleeve 24 can also be provided with a tear line 66 that extends across the width of the sleeve so as to permit easy access to the interior of the sleeve when desired. The tear line 66 can, if desired, extend across only a portion of the width of the sleeve 24.

Figure 5:
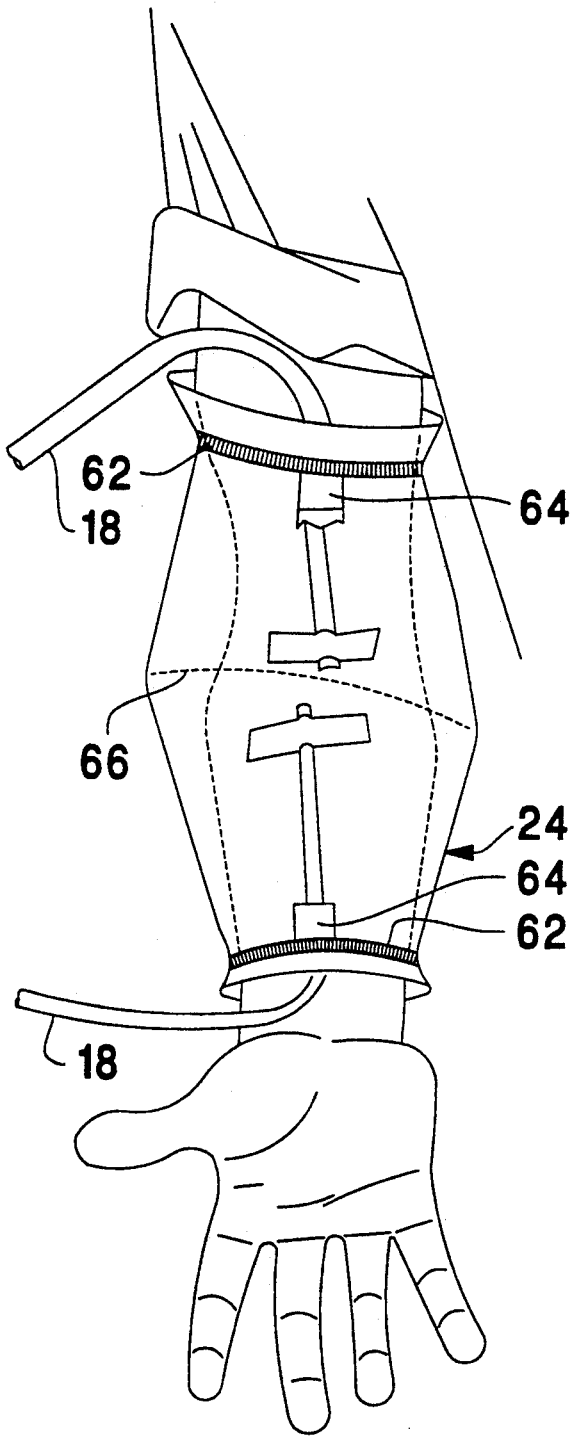
FIG. 5 is a plan view of the vascular access enclosure according to the present invention in use on a patient's arm.

Turning to FIG. 5 which illustrates the vascular access sleeve 24 in use on the arm of a patient, the sleeve 24 is positioned such that it surrounds and encloses the site of vascular access on the patient. Once in position, the blood tubing, and any other tubing, is mounted on the double tubing retainer 64. The elastic bands 62 on the ends of the sleeve 24 seal access through the openings 60 by tending to reduce the size of the openings 60 in the sleeve 24 so that the portion of the sleeve adjacent each end of the sleeve closely contacts and tightly surrounds the patient's arm as well as the blood tubing 18. In this way, a closed environment is defined within the interior of the sleeve 24 so that if a leak or rupture occurs at the site of vascular access, or if the tubing should become disconnected in the vicinity of the vascular access site, the resulting blood leak or rupture will be completely contained within the sleeve 24. As a result, individuals in the vicinity of the patient during the hemodialysis procedure will not be exposed to serious infectious diseases that may be present in the patient's blood.

From the foregoing, it can be appreciated that the dialyzer sleeve and the vascular access sleeve according to the present invention provide extremely effective solutions to the problem of contamination of the surrounding environment resulting from blood leakage and rupture during hemodialysis treatment. Consequently, the dialyzer sleeve and the vascular access sleeve afford protection to nearby patients that may not otherwise be adequately protected. Moreover, an additional form of protection is provided to those individuals wearing various protective garments. The sleeves 22, 24 are relatively simple and inexpensive to manufacture, yet extremely reliable in containing blood resulting from the occurrence of a rupture or leak during hemodialysis treatment.

Although FIG. 1 illustrates the dialyzer sleeve 22 and the access sleeve 24 as being used in conjunction with one another, it is understood that the sleeves could be used separate and independent from one another if desired. Because the sleeves are fabricated from a flexible and preferably light weight material, they can be easily employed during hemodialysis treatment. Additionally, in the case of the vascular access sleeve 24, little discomfort is experienced by the patient.

While the preferred embodiment of the dialyzer sleeve 22 and the access sleeve 24 have been described as being used during hemodialysis treatment, the sleeves 22, 24 are readily useable in conjunction with other types of medical procedures. The dialyzer sleeve 22 could be employed in connection with any type of extracorporeal medical device that involves the filtering of blood or other bodily fluids (e.g., plasmapheresis, heart/lung machines). Likewise, the access sleeve 24 has application in any type of medical procedure which requires access to a blood vessel in a portion of an individual's body, such as the arm or leg.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations, changes and equivalents may be made by others without departing from the spirit of the present invention. Accordingly, it is expressly intended that all such variations, changes and equivalents which fall within the spirit and scope of the present invention as defined in the claims, be embraced thereby.

What is claimed is:

1. In combination with an extracorporeal medical device for filtering bodily fluid that includes a housing, a bodily fluid inlet extending out of the housing through which bodily fluid flows to the extracorporeal medical device and a bodily fluid inlet extending out of the housing through which filtered bodily fluid flows from the extracorporeal medical device, an enclosure for enclosing the extracorporeal medical device, said enclosure comprising a sleeve having an interior, said sleeve surrounding the housing of the extracorporeal medical device so that the extracorporeal medical device is located in the interior of the sleeve to thereby contain bodily fluid resulting from the occurrence of a rapture during a medical procedure.

2. The combination according to claim 1, wherein said bodily fluid inlet is connected to tubing through which can be conveyed bodily fluid from a patient to the extracorporeal medical device and said bodily fluid outlet is connected to tubing through which filtered bodily fluid flowing out of the extracorporeal medical device can be returned to the patient, said sleeve having two oppositely positioned openings, said tubing that is connected to the bodily fluid inlet extending through one of the openings in the sleeve and the tubing that is connected to the bodily fluid outlet extending through the other opening in the sleeve, each of the two openings in the sleeve being provided with means for closing the opening so that a portion of the sleeve adjacent each opening contacts and tightly surrounds the tubing to thereby inhibit bodily fluid from escaping from the interior of the sleeve.

3. The combination according to claim 2, including a tubing retainer attached to an inner surface of the sleeve adjacent each of the two openings, each of the said tubings being retained in a corresponding one of the tubing retainers.

4. The combination according to claim 2, wherein said extracorporeal medical device includes a filtering fluid inlet through which filtering fluid flows into the extracorporeal medical device and a filtering fluid outlet through which filtering fluid flows out of the extracorporeal medical device, said sleeve being provided with two ports that extend through the sleeve along one side of the sleeve, said filtering fluid inlet extending through one of the ports in the sleeve and the filtering fluid outlet extending through the other one of the ports in the sleeve.

5. The combination according to claim 1, wherein said sleeve includes a tear line extending across at least a portion of the sleeve for permitting access to the interior of the sleeve.

6. The combination according to claim 1, wherein said sleeve is fabricated from a flexible, transparent plastic material.

7. The combination according to claim 1, wherein said extracorporeal medical device is a hemodialysis filter unit.

8. The combination according to claim 1, wherein said sleeve has oppositely positioned open ends that define two openings in the sleeve through which extend tubing connected to the extracorporeal medical device.

9. The combination according to claim 8, wherein said openings extend across the entire width of the sleeve.

10. The combination according to claim 1, wherein said sleeve is made of flexible material.

11. A medical enclosure used in conjunction with an extracorporeal medical device which possesses a housing for containing bodily fluid resulting from the occurrence of a rupture or leak during medical treatment, comprising a sleeve having an interior for receiving the housing of the medical device so that the sleeve surrounds and encloses the housing of the medical device, said sleeve having oppositely positioned ends that are open to define two openings for allowing tubing connected to the medical device to extend out of the sleeve, each of said two openings being provided with means for closing the opening once the medical device is positioned in the interior of the sleeve so that the portion of the sleeve adjacent each of the openings contacts and closely surrounds the tubing extending through each respective opening, and two ports extending through the sleeve for allowing a first fluid inlet and a first fluid outlet extending from the medical device to be connected to tubing.

12. The medical enclosure according to claim 11, including a tear line extending across at least a portion of the sleeve for allowing access to the interior of the sleeve.

13. The medical enclosure according to claim 11, including two tubing retainers secured to an inner surface of the sleeve, one of the tubing retainers being positioned adjacent one of the openings in the sleeve and the other tubing retainer being positioned adjacent the other opening in the sleeve, each of the tubing retainers comprising a substantially C-shaped member that encircles at least a portion of an outer surface of the tubing to retain the tubing in place within the interior of the sleeve.

14. The medical enclosure according to claim 11, wherein said sleeve is fabricated of a flexible, transparent plastic material.

15. The medical enclosure according to claim 11, wherein said means for closing each opening in the sleeve includes an adhesive strip positioned on an inner surface of the sleeve adjacent each of said openings.

16. The combination according to claim 11, wherein the oppositely positioned ends of the sleeve are open across the entire width of the sleeve.

17. The combination according to claim 11, wherein said sleeve is made of flexible material.

18. In combination with an extracorporeal medical device for filtering bodily fluid that includes a bodily fluid inlet through which bodily fluid flows to the extracorporeal medical device and a bodily fluid outlet through which filtered bodily fluid flows from the extracorporeal medical device, an enclosure for enclosing the extracorporeal medical device, said enclosure comprising a sleeve having an interior, said sleeve surrounding the extracorporeal medical device so that the extracorporeal medical device is located in the interior of the sleeve to thereby contain bodily fluid resulting from the occurrence of a rupture during a medical procedure, said sleeve including a tear line extending across at least a portion of the sleeve for permitting access to the interior of the sleeve.

* * * * *